United States Patent [19]

Zaiger et al.

[11] Patent Number: Plant 5,821

[45] Date of Patent: Dec. 9, 1986

[54] PEACH TREE (WHITE LADY)

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 697,871

[22] Filed: Feb. 4, 1985

[51] Int. Cl.[4] ..... A01H 5/03

[52] U.S. Cl. ..... Plt./42

[58] Field of Search ..... Plt./42

*Primary Examiner*—Robert E. Bagwill

[57] ABSTRACT

A new and distinct variety of peach tree which is of large size, medium dense, vigorous and upright in growth and a productive and regular bearer of large size, white flesh, freestone fruit having a high degree of red skin color. The fruit is further characterized by uniform ripening, coloring 7 to 10 days before maturity, very firm flesh and having more attractive red skin color than most white flesh peach varieties.

1 Drawing Figure

ORIGIN OF THE VARIETY

The new variety of peach tree was originated by us in the experimental orchard located at Modesto, Calif., as a first generation seedling from a cross between two selections. The maternal parent was a selection from a cross between O'Henry Peach (U.S. Plant Pat. No. 2,964) and Giant Babcock Peach (U.S. Plant Pat. No. 1,353) and the pollen parent originated from a cross of May Grand Nectarine (U.S. Plant Pat. No. 2,794) and Sam Houston Peach (Non-patented).

ASEXUAL REPRODUCTION OF THE VARIETY

Our new variety of peach tree was asexually reproduced by budding in the experimental orchard located at Modesto, Calif. and shows that all characteristics are established and transmitted through succeeding generations and come true to the original tree in all respects.

SUMMARY OF THE VARIETY

The new discovery relates to a distinct variety of peach tree which has the following unique combination of desirable features:

1. Fruit with very firm flesh.
2. Fruit with a high degree of red skin color.
3. Uniform maturity of fruit.
4. Large size of the fruit.
5. Coloring of the fruit 7 to 10 days before ripening.
6. Heavy and regular production of fruit.

PHOTOGRAPHS OF THE VARIETY

The accompanying photographs show typical specimens of the fruit and foliage of the new variety, with upper and lower surface of the leaves being illustrated and typical specimens of the fruit with an exterior and a sectional view being shown with the stone remaining in place. These photographs were taken shortly after being picked at maturity (shipping ripe) and the colors are as nearly true as possible in a color representation of this type.

DESCRIPTION OF THE VARIETY

The following is a detailed botanical description of the new variety of peach tree, with color terminology (except those in common terms) in accordance with Reinhold Color Atlas by A. Korneruf and J. H. Wanscher.

Tree:
- *Size.*—Large.
- *Vigor.*—Vigorous.
- *Growth.*—Upright.
- *Density.*—Medium dense.
- *Production.*—Productive.
- *Bearer.*—Regular.

Trunk:
- *Size.*—Medium to stocky.
- *Texture.*—Medium to shaggy.

Branches:
- *Size.*—Medium.
- *Surface.*—Smooth to medium rough.
- *Lenticels.*—Medium size. Medium number.
- *Color.*—Brown to grayish brown.

Leaves:
- *Size.*—Large. Average length — $6\frac{1}{2}''$. Average width — $1\frac{3}{4}''$.
- *Form.*—Lanceolate. Acutely pointed.
- *Thickness.*—Medium.
- *Texture.*—Smooth.
- *Margin.*—Crenate.
- *Petiole.*—Medium length.
- *Glands.*—Average number 4. Number varies from 2 to 6. Located on base of leaf and upper portion of petiole. Reniform.
- *Color.*—Upper surface — green (27-E-8) to deep green (27-F-8). Lower surface — dull green (27-E-4) to (27-E-5).

Flower buds:
- *Size.*—Large.
- *Length.*—Medium.

Flowers:
- *Blooming period.*—Mar. 1, 1982 to Mar. 7, 1982. Varies slightly due to weather variations.
- *Size.*—Large, showy.
- *Color.*—Pink.
- *Pollen.*—Present.

Fruit:
- *Maturity when described.*—Hard ripe.
- *Date of first picking.*—July 10, 1982.
- *Date of last picking.*—July 15, 1982.
- *Size.*—Large. Average axial diameter — $2\frac{7}{8}''$. Average transversely in suture plane — $3''$.
- *Form.*—Globose — nearly symmetrical.
- *Suture.*—Shallow — extends from base to apex.

*Ventral surface.*—Rounded — only slightly lipped.
*Apex.*—Rounded to slightly depressed.
*Cavity.*—Rounded to slightly elongated in suture plane. Average depth — 7/16". Average breadth — ¾".

Skin:
*Thickness.*—Medium.
*Texture.*—Medium. Tenacious to flesh.
*Down.*—Moderate to heavy. Moderate in length.
*Tendency to crack.*—None.
*Color.*—Light yellow ground color — (3-A-5) to yellowish white (3-A-2). Overspread with red (8-A-8 to 9-A-8).

Flesh:
*Color.*—White to oyster white (2-A-1 to 2-A-2). Stone cavity — tile red to reddish orange (7-A-7 to 7-A-8).
*Texture.*—Very firm.
*Fibers.*—Few, tender.
*Ripens.*—Evenly.
*Eating quality.*—Very good.
*Flavor.*—Sub-acid — very mild.
*Amygdalin.*—Undetected.
*Juice.*—Moderate.
*Aroma.*—Moderate.

Stone:
*Type.*—Freestone.
*Size.*—Large. Average length — 15/16". Average width — 15/16". Average thickness — 9/16".

*Form.*—Ovid.
*Apex.*—Acuminate.
*Base.*—Straight to slightly oblique.
*Sides.*—Equal to unequal.
*Surface.*—Furrowed toward apex and pitted toward base.
*Ridges.*—Rounded.
*Tendency to split.*—Very slight.
*Color.*—Brown to mahogany brown (8-D-6 to 8-D-7).

Use: Dessert. Market.
Keeping quality: Good.
Storage quality: Good.

The new and distinct variety of peach tree and its fruit described above may vary in slight detail due to climatic, soil and cultural practices under which the variety may be grown; the present description being that of the new variety grown under the ecological conditions prevailing at Modesto, Calif.

The following is claimed:

1. A new and distinct variety of peach tree which is of large size, vigorous, upright in growth and a regular and productive bearer of large, very firm, white flesh, freestone fruit with very good eating quality; the fruit is further characterized by coloring 7 to 10 days before maturity and having more attractive red skin color than most other white fleshed commercial varieties.

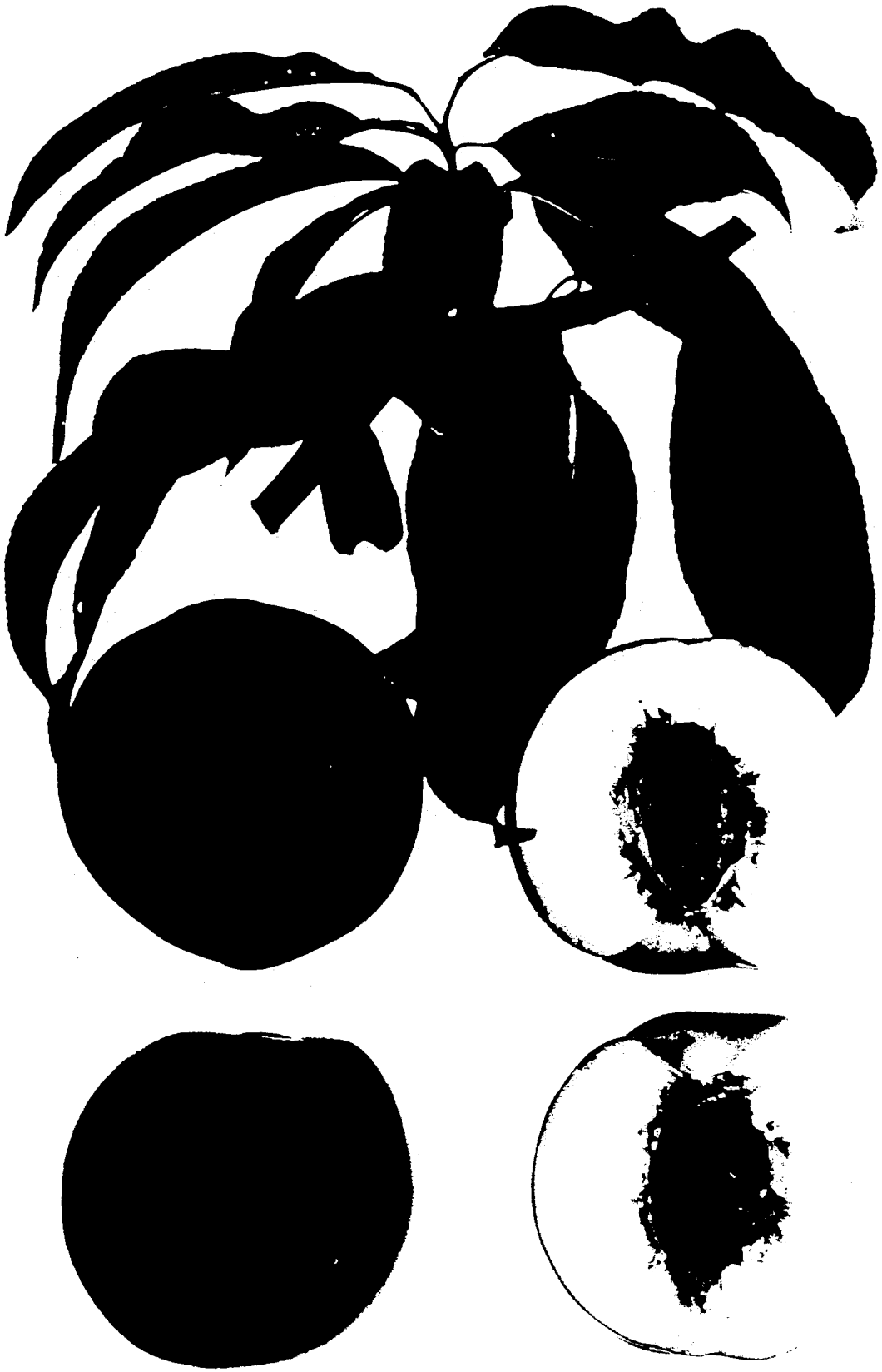

* * * * *